United States Patent [19]

Randklev

[11] Patent Number: 4,808,228
[45] Date of Patent: Feb. 28, 1989

[54] GLASS IONOMER CEMENT POWDER

[75] Inventor: Ronald M. Randklev, White Bear Lake, Minn.

[73] Assignee: Minnesota Mining and Manufacturing Company, St. Paul, Minn.

[21] Appl. No.: 17,058

[22] Filed: Feb. 20, 1987

[51] Int. Cl.$^4$ .......................... A61K 6/02; A61K 6/06; A61K 6/08

[52] U.S. Cl. .................................. 106/35; 260/998.11; 433/228.1; 523/116; 523/118

[58] Field of Search .................. 106/35; 523/109, 116, 523/118; 433/228.1; 260/998.11

[56] References Cited

U.S. PATENT DOCUMENTS

| | | | |
|---|---|---|---|
| 3,655,805 | 4/1972 | Croce et al. | 260/680 |
| 3,814,717 | 6/1974 | Wilson et al. | 260/29.6 |
| 4,016,124 | 4/1977 | Crisp et al. | 260/29.6 |
| 4,089,830 | 5/1978 | Tezuka et al. | 260/29.6 |
| 4,131,481 | 12/1978 | Drake et al. | 106/122 |
| 4,143,018 | 3/1979 | Crisp et al. | 260/29.6 |
| 4,209,434 | 6/1980 | Wilson et al. | 260/29.6 |
| 4,222,920 | 9/1980 | Crisp et al. | 260/29.6 |
| 4,317,681 | 3/1982 | Beede et al. | 106/85 |
| 4,360,605 | 11/1982 | Schmitt et al. | 523/116 |
| 4,373,936 | 2/1983 | Tomioka et al. | 523/116 |
| 4,376,835 | 3/1983 | Schmitt et al. | 523/116 |
| 4,438,212 | 3/1984 | Potter et al. | 501/73 |
| 4,527,979 | 7/1985 | McLean et al. | 523/116 |

OTHER PUBLICATIONS

Prosser et al., NMR Spectroscopy of Dental Materials. II, "The Role of Tartaric Acid in Glass-Ionomer Cements", *J. Bio. Mat. Res.*, 16, 431–445 (1982).

"Size Reduction", *Kirk-Othmer Enclopedia of Chemical Technology*, 3rd Ed., 21, 132–161 (1983).

*Primary Examiner*—Paul Lieberman
*Assistant Examiner*—Linda D. Skaling
*Attorney, Agent, or Firm*—Donald M. Sell; David R. Cleveland

[57] ABSTRACT

Carboxylic acids are comminuted with fluoroaluminosilicate glass frit to form a cement powder containing carboxylate salt. The cement powder can be used to prepare glass ionomer dental cements with extended work times.

8 Claims, 5 Drawing Sheets

GLASS IONOMER CEMENT POWDER

TECHNICAL FIELD

This invention relates to glass ionomer cement powders, and to a process for making such powders.

BACKGROUND OF THE INVENTION

Dental cements of the so-called "glass-ionomer" variety are formed by reacting a fluoroaluminosilicate glass powder ("glass") and a poly(carboxylic acid) ("polyacid") in the presence of water. The mixture undergoes a brief working period, during which the reactants are converted from a creamy paste to a relatively firm, carvable solid. The working period is followed by a brief setting period, during which the carvable solid becomes sufficiently strong to function as a dental cement. The cured cement provides an ion-leachable source of fluoride with beneficial cariostatic properties. Work time, set time and mix viscosity of the cement are each important to the user, and tend to govern market acceptability of the cement. Most dentists prefer longer work times and faster set times. Unfortunately, when set times are accelerated by the usual methods, work times are also reduced.

Virtually all commercially available glass ionomer cements include a chelating agent (usually tartaric acid) that adjusts the work time and set time of the cement. Such chelating agents are described in U.S. Pat. Nos. 4,209,434, 4,089,830, 4,317,681 and 4,374,936, and in Prosser et al., "NMR Spectroscopy of Dental Materials. II. The role of Tartaric Acid in Glass-Ionomer Cements", *J. Bio. Mat. Res.*, 16, 431–445 (1982).

Work time and set time can also be adjusted by controlling the particle size and surface area of the glass; by treating the glass with an acid, thoroughly washing the treated glass to leave substantially no soluble calcium salts on the surface of the glass particles, and drying the washed particles (U.S. Pat. No. 4,376,835); by controlling the molecular weight and carboxyl equivalent weight of the polyacid; or by controlling the ratio of glass to polyacid.

SUMMARY OF THE INVENTION

Further adjustability of work time and set time would be desirable in order to provide more leeway in the formulation of glass ionomer cements and to extend their practical application to uses involving higher glass loading levels (e.g., for posterior or incisal applications) or lower mix viscosity (e.g., for endodontic sealants) than are attainable using current techniques. The present invention provides, in one aspect, a glass ionomer cement powder having a desirable combination of work time, set time, and mix viscosity. The powder comprises an intimate, substantially anhydrous mixture of finely divided fluoroaluminosilicate glass and carboxylic acid, said powder containing carboxylate salt.

The present invention also provides a process for making such a cement powder, by comminuting the glass and the carboxylic acid together under sufficiently vigorous, substantially anhydrous pulverization conditions (e.g., ball milling) to form carboxylate salt in the powder. Ordinary dry mixing (e.g., using a twin shell blender) is not sufficient to accomplish such process. Mixing in the presence of moisture can result in carboxylate salt formation but entrains water in the cement, resulting in poor mix properties and shortened work times.

DETAILED DESCRIPTION

Figure 1:
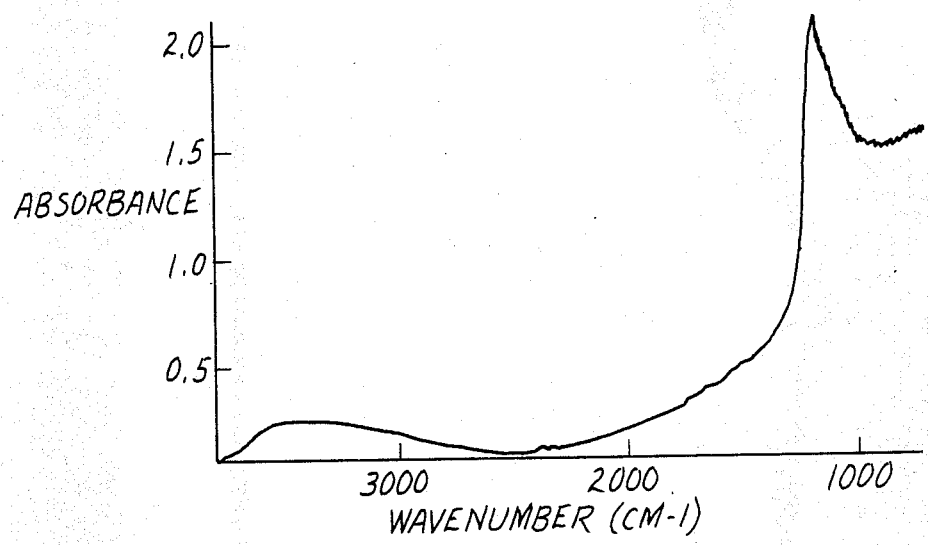
FIGS. 1–7 are Diffuse Reflectance Fourier Transform Infrared ("DRFTIR") spectra for the cement powders of COMPARISON EXAMPLE 1, EXAMPLES 1, 2, 4, and 5 and COMPARISON EXAMPLES 2 and 3, respectively.
Figure 2:
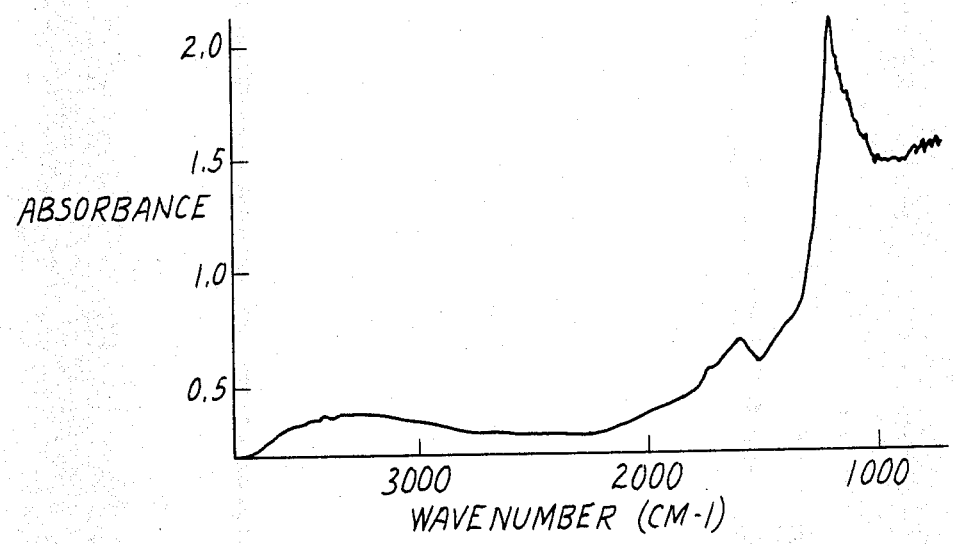
Figure 3:
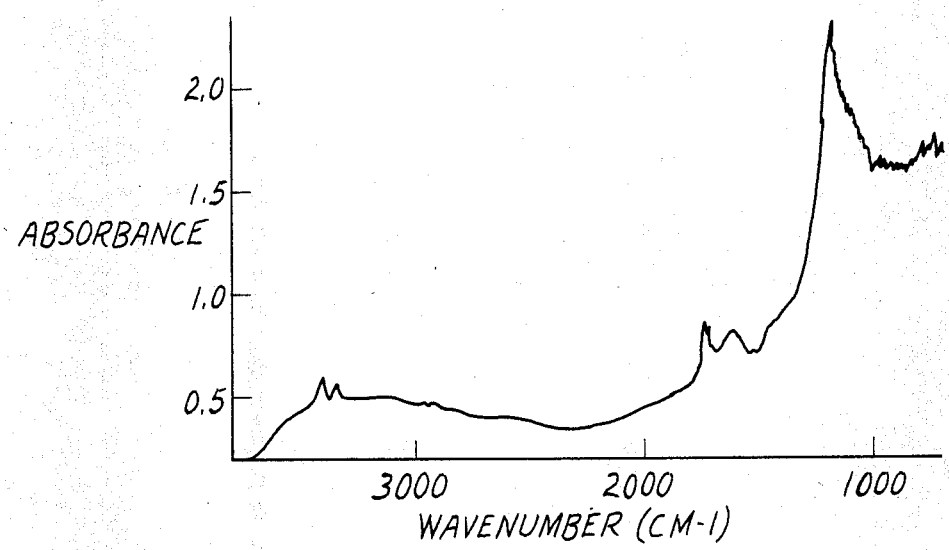
Figure 4:
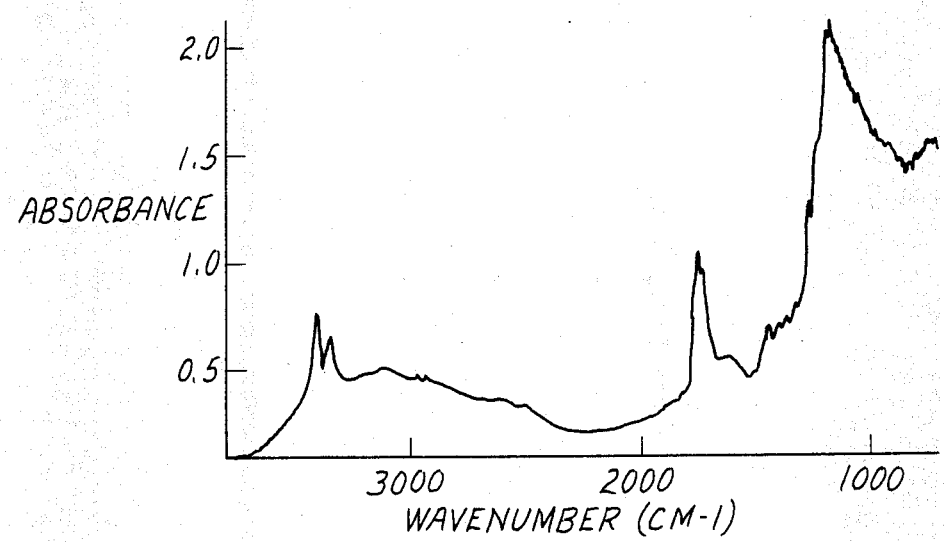
Figure 5:
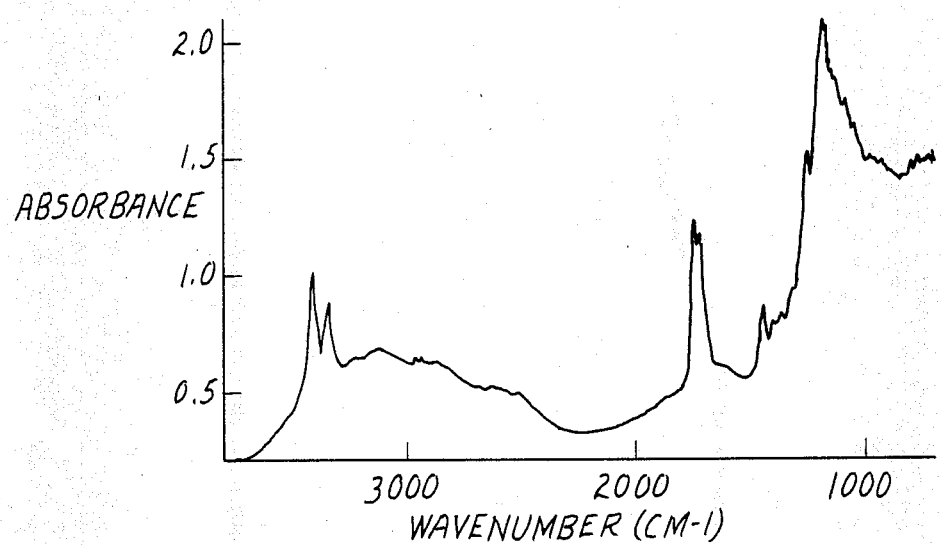

Fluoroaluminosilicate glasses for use in the present invention are those glass powders that when combined with a conventional polyacid react to for a glass ionomer dental cement capable of supplying fluoride by ion leaching. Representative glasses are described in U.S. Pat. Nos. 3,814,717, 4,143,018, 4,209,434, 4,360,605 and 4,376,835. The polyacid usually contains many (e.g., 100 or more) carboxyl groups per molecule and is described in the same patents and in U.S. Pat. Nos. 3,655,805, 4,016,124, 4,089,830, 4,222,920 and 4,374,936.

The glass should have a particle diameter suitable for use in dentistry. Preferably, the glass particles are sufficiently finely divided so that their maximum particle diameter is below about 100 micrometers, more preferably below about 50 micrometers. The particle size and size distribution of the glass can be adjusted using conventional techniques (e.g., grinding, screening, sedimentation or other particle classification methods) in order to influence the strength, work time and set time of the cement.

Carboxylic acids for use in the cements of the present invention are those water-soluble carboxylic acids that serve as chelating agents and retard the set time of the glass. The carboxylic acid should have a physical state that facilitates comminution with the glass under vigorous, anhydrous pulverization conditions as described in more detail below. Although the carboxylic acid can be a liquid or a solid, and, if desired, can be the polyacid itself, preferably the carboxylic acid is solid mono-, di-, tri- or tetra-carboxylic acid. More preferably the carboxylic acid is a dicarboxylic acid, and most preferably it is tartaric acid. Tartaric acid can be used in its meso- or l-isomer forms, but preferably is used in its d- (otherwise known as "L" or "(2R, 3R)-(+)") or d,l-isomer forms. Other suitable carboxylic acids include succinic acid, malic acid, maleic acid, itaconic acid, citraconic acid, ethylenediaminetetraacetic acid, propanetricarboxylic acid, citric acid, aconitic acid, salicylic acid and mellitic acid. Additional suitable carboxylic acids are described in U.S. Pat. Nos. 4,209,434, 4,089,830, 4,317,681, and 4,374,936, and in the Prosser et al. article cited above.

Sufficient carboxylic acid should be employed to obtain the desired work time or set time. Preferably, the carboxylic acid should be added in an amount sufficient to extend the work time by at least 15 seconds. Low amounts of carboxylic acid (e.g., about 1 weight percent or less based on the weight of the glass) will extend work time without substantially affecting set time. Larger amounts (e.g., above about 1%) will extend both work time and set time. As a general guide, a preferred amount of carboxylic acid is about 0.1 to about 10%, more preferably about 0.25 to about 7%, based on the weight of the glass. Large amounts of carboxylic acid (e.g., about 5% or more) should be used for applications (e.g., endodontic sealants or bone cements) where long set times are desired, and for applications (e.g., basing cements, crown build-up cements or posterior liners) where high glass loading levels are desired. Lower amounts of carboxylic acid (e.g., about 3% or less) should be used for applications (e.g., luting cements, veneer cements or orthodontic bracket adhesives) where rapid set time is desired.

The carboxylic acid and glass should be combined under substantially anhydrous conditions, i.e., in the substantial absence of water. Addition of water to the glass, even if followed by a drying step, tends to promote the irreversible incorporation or entrainment of water in the cement powder, thereby causing an undesirable reduction in work time and poor mixing and flow properties when the cement powder and polyacid are combined.

The glass and carboxylic acid are comminuted together under conditions that involve sufficient impact energy to cause reaction between the glass and carboxylic acid and formation of carboxylate salt in the cement powder. Suitable comminution means are described in "Size Reduction", *Kirk-Othmer Encyclopedia of Chemical Technology*, 3d. Ed., 21, 132–161 (1983). Impact comminution means that employ media are preferred, such as tumbling mills (e.g., ball mills), attrition mills, and vibration mills. Ball milling is particularly preferred. Added heat or pressure can be employed to promote the reaction. Formation of carboxylate salt can be detected using a variety of analytical techniques, e.g., NMR (see the Prosser et al. article cited above) and DRFTIR. DRFTIR is particularly preferred. It can be used to detect the carboxylate salt absorption peaks that occur at about 1610–1550 $cm^-$ (asymmetric stretching) and about 1400 $cm^-$ (symmetric stretching).

Figure 7:
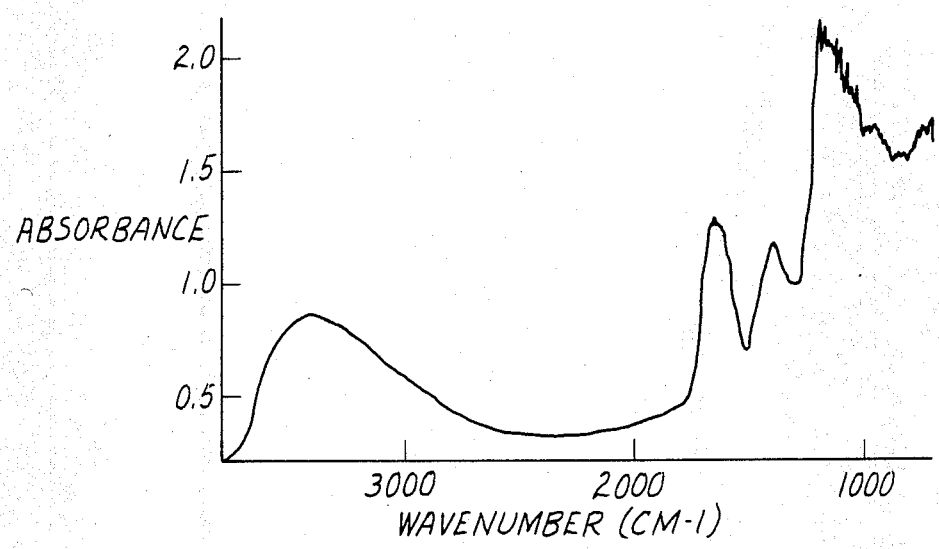

The glass and carboxylic acid will also react to form carboxylate salt if they are mixed under moist conditions. As noted above, this causes entrainment of water in the glass, undesirably speeds up set time, and harms mixing and flow properties. The presence of moisture can be detected using a variety of analytical techniques. For example, DRFTIR can be used to detect the broad water absorption peak at about 3500 $cm^-$ (see FIG. 7).

When it is desired to prepare the cured cement, the cement powder should be mixed with a conventional aqueous polyacid (i.e., acrylic acid copolymer) solution of the type commonly used to form glass ionomer cements. If desired, the polyacid can be dried (e.g., by freeze-drying) and the resulting dried copolymer mixed with the cement powder of the invention. Addition of water to the resulting mixture will form a cured dental cement.

If desired, the cement powder can contain or be combined with adjuvants such as pigments, viscosity modifiers (e.g., microfine silica at preferred amounts of 2 to 10 weight percent based on the weight of the glass), wetting agents, milling agents, extending fillers, radiopacifiers, metal powders (e.g., silver or silver alloys), medicaments and the like.

Because the cement powder of the invention can be formulated to provide a wide latitude in work and set times, corresponding wide adjustments in the reactivity of the glass or the polyacid can also be sought or tolerated. This enables practical application of the cement powder of the invention in dental applications where glass ionomer cements have not heretofore been successfully commercially employed. Such applications include endodontic sealants (where very long work times are desired) and highly-filled glass ionomer cements (where very high powder loadings and very fine glass particle sizes are desired to impart strength to the cured cement). The invention also enables improved latitude in the mixing ratio of the cement powder and polyacid without undue shortening of the work time. In addition, the cement powder has improved mixing characteristics when it is combined with the polyacid, resulting in reduced mixing time and consequently greater useful work time. Tartaric acid, if used as the carboxylic acid, also functions as a milling aid resulting in faster pulverization of the glass frit.

The invention is further illustrated in the following examples, in which all parts and percentages are by weight unless otherwise indicated.

EXAMPLES 1–6 and COMPARISON EXAMPLE 1

A fluoroaluminosilicate glass frit was prepared by fusing together and then cooling the following ingredients:

| Ingredient | Parts |
|---|---|
| $La_2O_3$ | 38.20 |
| $SiO_2$ | 18.22 |
| $CaF_2$ | 12.50 |
| $AlF_3$ | 11.00 |
| $Al_2O_3$ | 10.60 |
| $Na_2AlF_6$ | 5.88 |
| $P_2O_5$ | 2.60 |
| MgO | 1.00 |

The glass frit was combined with varying amounts of d-tartaric acid and milled, using 12 mm×12 mm alumina rod media, in a ceramic mill jar rotated at 60 rpm for 4 hours, until cement powder particles having an average particle diameter of 4.7 micrometers (measured using sedigraph analysis) were obtained.

Figure 8:
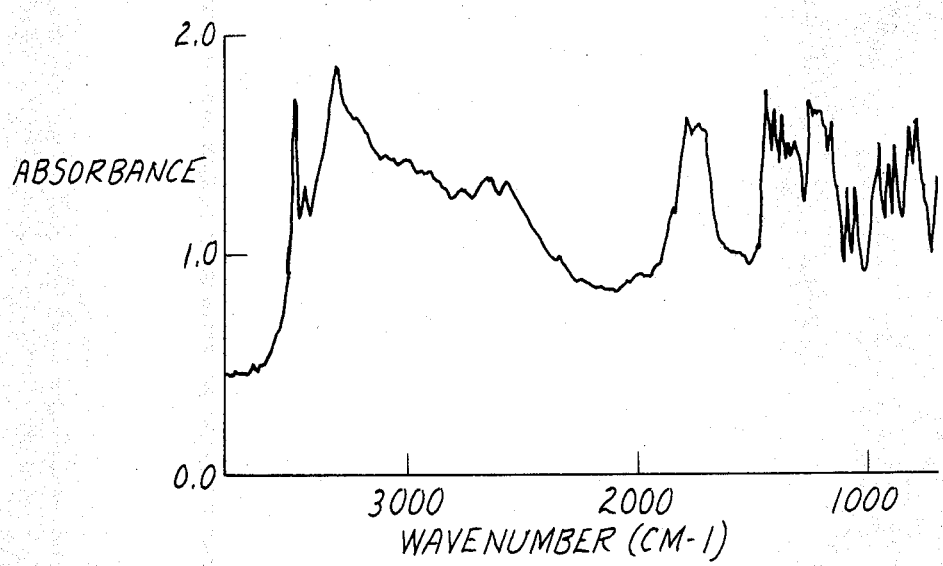
FIG. 8 is a DRFTIR spectrum for tartaric acid.

DRFTIR spectra for several of the milled cement powders were obtained using an IBM Model 9420 infrared spectrophotometer. The spectra for COMPARISON EXAMPLE 1 and EXAMPLES 1, 2, 4, and 5 are reproduced as FIGS. 1–5, respectively. The DRFTIR spectrum for d-tartaric acid is shown in FIG. 8. FIGS. 1–5 illustrate the virtual absence of distinct absorption peaks for carboxylate salt in the cement powder of COMPARISON EXAMPLE 1 (no tartaric acid), and the appearance of carboxylate salt absorption peaks in the cement powders of EXAMPLES 1, 2, 4 and 5 (0.5, 1.0, 4.0 and 5.0% tartaric acid, respectively). The carboxylate salt peaks appear to reach a saturated value at about 0.5 to 1% tartaric acid. At tartaric acid addition levels above about 1% the carboxylic acid absorption peaks (about 1765–1710 $cm^-$) increase with increased tartaric acid addition levels, while the carboxylate salt peaks remain relatively unchanged. These peaks can also be observed using difference spectra obtained by standard subtractive techniques.

An aqueous polyacid solution was prepared by polymerizing a 4:1:0.4 molar ratio mixture of acrylic acid:itaconic acid:/acrylamidoglycolic acid in water. The resulting polyacid was a 46–48% solids aqueous solution with a number average molecular weight of 5500.

The milled cement powders and polyacid were mixed at a 1.4:1 powder:liquid mix ratio and hand spatulated at room temperature until a homogeneous mixture was obtained. The time required to obtain homogeneity was recorded as the mix time. The mixing and flow properties of the cement were also subjectively evaluated. A "heavy mix" was difficult to mix and had a consistency like honey. A "creamy mix" was easy to mix and had a consistency like corn oil or dairy cream. A cement with "poor flow" exhibited manually detectable resistance to spreading and did not readily wet out a glass slab or paper mixing pad. A cement with "excellent flow" exhibited no detectable resistance to spreading and rapid wetting properties. A cement with "good flow" had spreading and wetting characteristics intermediate between cements with poor or excellent flow. Work time was evaluated by applying a small quantity of cement to a fingernail using a ball applicator dental instrument and smearing the cement to form a continuous film. This procedure was repeated every 15 seconds using a new quantity of cement, until the cement became excessively stringy or a discontinuous film was formed. The time period from the completion of mixing until the last satisfactory film was formed was recorded as the work time. Set time was evaluated using ISO specification 7489-1986(E), procedure 6.3.

Set out below in Table I are the comparison example number or example number, the amount of tartaric acid added to the ball mill, the time required for complete mixing of the cement, the work time, the set time, and comments regarding the handling characteristics of each cement.

TABLE I

| COMPARISON EXAMPLE NO. or EXAMPLE NO. | % Tartaric acid added to ball mill | Time required to mix | Work time | Set time | Comments |
| --- | --- | --- | --- | --- | --- |
| Comp. Ex. 1 | 0 | 30 sec. | 10-15 sec. | 5 min. | Heavy mix; poor flow |
| Ex. 1 | 0.5 | 20 sec. | 45 sec. | 5 min. | creamy mix; good flow |
| Ex. 2 | 1.0 | 20 sec. | 45 sec. | 5 min. | creamy mix; good flow |
| Ex. 3 | 3.0 | 15 sec. | 1 min. 35 sec. | 6 min. | creamy mix; excellent flow |
| Ex. 4 | 4.0 | 15 sec. | 3 min. | 8 min. | creamy mix; excellent flow |
| Ex. 5 | 5.0 | 15 sec. | 3 min. 45 sec. | 11 min. | creamy mix; excellent flow |
| Ex. 6 | 10.0 | 15 sec. | 11 min. | 40 min. | creamy mix; excellent flow |

The above data illustrates the effect of addition of tartaric acid to the ball mill during frit pulverization. As the amount of tartaric acid was increased, the milled cement powder became easier to mix with the polyacid, the flow properties of the mixture improved, and work time increased. At tartaric acid levels above 1%, set time also increased.

Several dental products were prepared by combining the cement powders of EXAMPLES 1, 3, 4 or 5 with the polyacid used in these EXAMPLES 1-6 ("Liquid A") or with a polyacid containing a conventional chelating agent solution ("Liquid B", containing 10% tartaric acid dissolved in Liquid A). Set out below in Table II are the ingredients in these dental products, the powder:liquid mix ratio, the mix time, work time and set time and suggested uses for each product.

TABLE II

| Cement powder of EXAMPLE | Polyacid | Powder: liquid ratio | Time required to mix | Work time | Set time | Suggested use |
| --- | --- | --- | --- | --- | --- | --- |
| 1 | Liquid B | 1.4:1 | 15 sec. | 85 sec. | 5 min. | Cavity liner |
| 3 | Liquid B | 1.4:1 | 15 sec. | 2 min. 30 sec. | 7 min. | Crown, bridge and orthodontic cement |
| 4 | Liquid A | 1.4:1 | 15 sec. | 3 min. | 8 min. | Luting cement |
| 5 | Liquid B | 1.2:1 | 15 sec. | 7 min. | 16 min. | Endodontic sealant |
| 5 | Liquid B | 4:1 | 15 sec.[1] | [2] | 7 min. | Crown buildup base |
| 5 | Liquid B | 5:1 | 15 sec.[1] | [2] | 6 min. | Posterior base. |

[1]Mixed in an amalgam triturator capsule, using a standard amalgamator.
[2]Heavy putty-like consistency until set.

Figure 9:
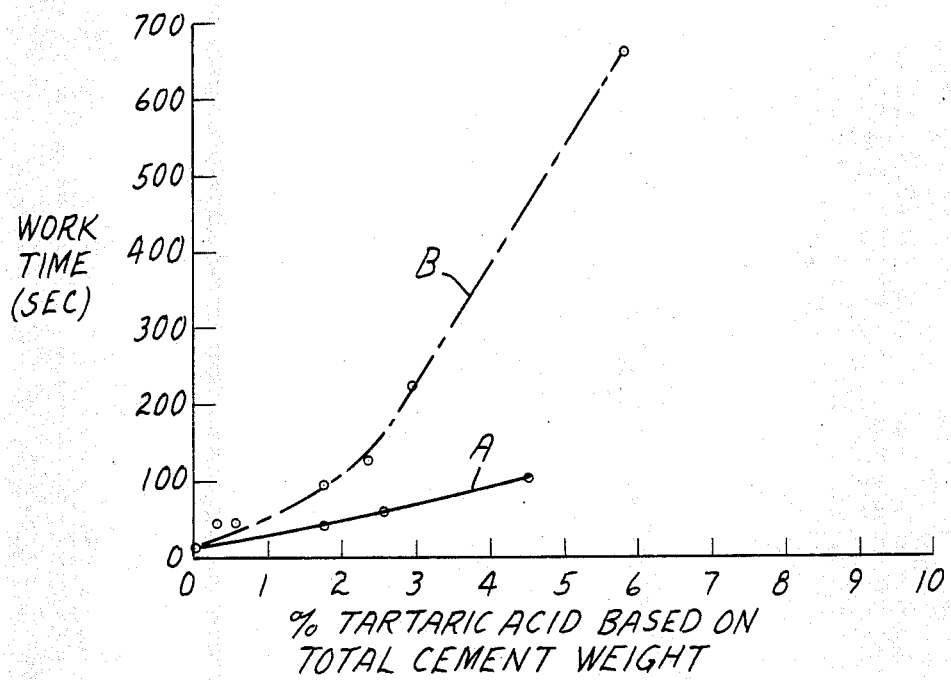
FIG. 9 is a plot of the amount of tartaric acid vs. work time for two methods of addition of tartaric acid to a glass ionomer cement powder.

In a further comparison, varying amounts (5%, 10%, 15% and 30%, based on the weight of polyacid) of tartaric acid were dissolved in the polyacid solution, then mixed with the glass of COMPARISON EXAMPLE 1 (no tartaric acid). For each of the resulting cement mixtures, the percentage of tartaric acid (based on the total weight of cement) was plotted against work time. A curve (shown in FIG. 9, and labelled "A") was drawn through the data points. Also shown in FIG. 9 is a curve (labelled "B") that plots the percentage of tartaric acid (based on the total weight of cement) against work time for EXAMPLES 1-6. Comparison of curves A and B demonstrates that the cement powders of the present invention are more efficiently chelated than conventional cements. In other words, at equivalent tartaric acid addition levels, the work time of the cement powder of the present invention is more prolonged than the work time of a cement made using a conventional solution of tartaric acid in the liquid portion of the cement.

COMPARISON EXAMPLE 2

Figure 6:
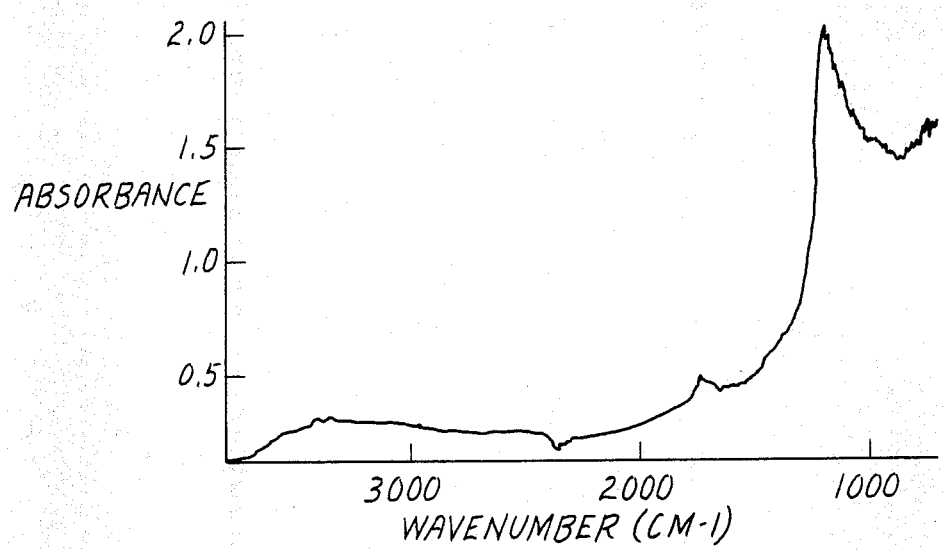

A portion of the ball milled glass of COMPARISON EXAMPLE 1 (no tartaric acid) was mixed with 5% tartaric acid using a twin shell blender, until a homogeneous powder was obtained. The DRFTIR Spectra of the cement powder (FIG. 6) exhibited characteristic tartaric acid carboxyl group absorption peaks at about 1740 and 1725 cm$^-$, but no evidence of carboxylate salt absorption. When the cement powder was combined with polyacid as in EXAMPLES 1-6, 30 seconds were required for mixing. The cement had a work time of 65 seconds and a set time of 5 minutes, 30 seconds, values very close to those that would be obtained if an equivalent amount (7%) of tartaric acid was added to the polyacid. The above data thus illustrates that ordinary dry blending of the glass and tartaric acid is not sufficient to provide a cement powder of the present invention.

The dry blending procedure used in the above comparison example is believed to approximate the powder blending referred to in U.S. Pat. Nos. 4,209,434 and 4,317,681.

COMPARISON EXAMPLE 3

Nineteen parts of the milled glass powder of COMPARISON EXAMPLE 1 were combined with 1 part tartaric acid and 30 parts water to form a slurry. The slurry was stirred for fifteen minutes, dried in shallow pans in a 43° C. circulating air oven for 38 hours, manually repulverized, and screened through a nylon sieve with 74 micrometer openings. The DRFTIR Spectra of the resulting dried powder (FIG. 7) indicated the presence of water, thus suggesting that the powder was not substantially anhydrous. The dried powder was returned to the oven for 72 additional hours and then reexamined by DRFTIR. The spectrum exhibited no change, indicating that the water had become entrained in the powder. When the glass was combined with polyacid as in Examples 1-6, 30 seconds were required for mixing. The mixture was very heavy and had poor flow capabilities. The cement had a work time of 15-20 seconds and a set time of 5 minutes, 15 seconds. These work time and set time values were not substantially different from those obtained when no tartaric acid was present (Comparison Example 1). This is believed to have been due to the presence of the entrained water in the powder, which serves to accelerate the setting reaction.

Various modifications and alterations of this invention will become apparent to those skilled in the art without departing from the scope and spirit of this invention, and it should be understood that this invention is not limited to the illustrative embodiments set forth herein.

I claim:

1. A process for making a dental cement powder, comprising the step of comminuting together fluoroaluminosilicate glass and carboxylic acid under sufficiently vigorous, substantially anhydrous pulverization conditions to form carboxylate salt in said powder wherein the presence of said salt in said powder is detectable by a diffuse reflectance Fourier transform infrared spectrum that exhibits distinct absorption peaks between 1610-1550 cm$^-$ or at 1400 cm$^-$.

2. A process according to claim 1, wherein said pulverization conditions comprise impact comminution means that employ media.

3. A process according to claim 2, wherein said impact comminution means comprise a tumbling mill, attrition mill or vibration mill.

4. A process according to claim 2, wherein said impact comminution means comprise a ball mill.

5. A process according to claim 1, wherein said carboxylic acid comprises a solid mono-, di-, tri-, or tetracarboxylic acid.

6. A process according to claim 1, wherein said carboxylic acid comprises tartaric acid.

7. A process according to claim 6, wherein said tartaric acid comprises d-tartaric acid.

8. A process according to claim 1, wherein the amount of said carboxylic acid is sufficient to extend by at least 15 seconds the work time of a cement made by combining said glass with aqueous poly(carboxylic acid).

* * * * *

UNITED STATES PATENT AND TRADEMARK OFFICE
CERTIFICATE OF CORRECTION

PATENT NO. : 4,808,228
DATED : February 28, 1989
INVENTOR(S) : Ronald M. Randklev It is certified that error appears in the above-identified patent and that said Letters Patent is hereby corrected as shown below:

In Column 2, line 19, "for" should read --form--.

In Column 3, line 37, "cm-" should read --$cm^{-1}$--.

In Column 3, line 38, "cm-" should read --$cm^{-1}$--.

In Column 3, line 46, "cm-" should read --$cm^{-1}$--.

In Column 4, line 56, "cm-" should read --$cm^{-1}$--.

In Column 7, line 5, "cm-" should read --$cm^{-1}$--.

In Column 8, line 20, "cm-" should read --$cm^{-1}$--.

Signed and Sealed this

Twenty-sixth Day of September, 1989

Attest:

DONALD J. QUIGG

Attesting Officer

Commissioner of Patents and Trademarks